United States Patent
Xu et al.

(10) Patent No.: US 9,526,436 B2
(45) Date of Patent: Dec. 27, 2016

(54) AMPLIFIERS INCLUDING TUNABLE TUNNEL FIELD EFFECT TRANSISTOR PSEUDO RESISTORS AND RELATED DEVICES

(71) Applicant: Samsung Electronics Co., Ltd., Suwon-si, Gyeonggi-do (KR)

(72) Inventors: Nuo Xu, San Jose, CA (US); Jing Wang, San Jose, CA (US); Woosung Choi, Pleasanton, CA (US)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 14/729,339

(22) Filed: Jun. 3, 2015

(65) Prior Publication Data

US 2016/0338612 A1    Nov. 24, 2016

Related U.S. Application Data

(60) Provisional application No. 62/163,533, filed on May 19, 2015.

(51) Int. Cl.
*H03F 3/187* (2006.01)
*A61B 5/0482* (2006.01)
*H03F 1/02* (2006.01)
*H03F 3/45* (2006.01)

(52) U.S. Cl.
CPC .......... *A61B 5/0482* (2013.01); *H03F 1/0205* (2013.01); *H03F 3/45179* (2013.01); *H03F 2203/45116* (2013.01); *H03F 2203/45118* (2013.01)

(58) Field of Classification Search
CPC ................................. H03F 3/187; H03F 3/195
USPC ......................................... 330/307, 260, 261
See application file for complete search history.

(56) References Cited

U.S. PATENT DOCUMENTS

| | | | |
|---|---|---|---|
| 7,167,053 B2 | 1/2007 | Abadeer et al. | |
| 8,120,115 B2* | 2/2012 | Vandenberghe | B82Y 10/00 257/365 |
| 8,629,428 B2 | 1/2014 | Verhulst et al. | |
| 8,659,340 B2* | 2/2014 | Shiue | H03H 11/245 327/308 |
| 8,796,733 B2 | 8/2014 | Seabaugh et al. | |
| 8,860,160 B2 | 10/2014 | Cheng et al. | |
| 9,111,780 B2* | 8/2015 | Chuang | H01L 29/66356 |

(Continued)

FOREIGN PATENT DOCUMENTS

WO    WO 2012/152762 A1    11/2012

OTHER PUBLICATIONS

Ventatagirish Nagavarapu, et al, "The Tunnel Source (PNPN) n-MOSFET: A Novel High Performance Transistor," IEEE Transactions on Electron Devices, vol. 55, No. 4, Apr. 2008.

(Continued)

*Primary Examiner* — Henry Choe
(74) *Attorney, Agent, or Firm* — Myers Bigel, P.A.

(57) ABSTRACT

Neural signal amplifiers include an operational amplifier and a feedback network coupled between an output and an input thereof. The feedback network includes a tunnel field effect transistor ("TFET") pseudo resistor that exhibits bi-directional conductivity. A drain region of the TFET may be electrically connected to the gate electrode thereof to provide a bi-directional resistor having good symmetry in terms of resistance as a function of voltage polarity.

18 Claims, 8 Drawing Sheets

(56) References Cited

U.S. PATENT DOCUMENTS

| | | | |
|---|---|---|---|
| 2011/0140785 A1* | 6/2011 | Lian | H03F 3/187 330/293 |
| 2013/0090706 A1 | 4/2013 | Nudo et al. | |
| 2014/0093016 A1 | 4/2014 | Umeda et al. | |
| 2015/0206958 A1* | 7/2015 | Walke | H01L 29/66356 257/105 |
| 2015/0287802 A1* | 10/2015 | Lee | H01L 29/516 257/105 |
| 2015/0318214 A1* | 11/2015 | Tsai | H01L 21/82348 257/9 |
| 2015/0333534 A1* | 11/2015 | Liu | H02J 5/005 307/104 |

OTHER PUBLICATIONS

Sung Hwan Kim, et al, "Germanium-Source Tunnel Field Effect Transistors with Record High $I_{ON}/I_{OFF}$" 2009 Symposium of VLSI Technology Digest of Technical Papers.

Reid R. Harrison, et al, "A Low-Power Integrated Circuit for Wireless 100-Electrode Neural Recording System," IEEE Journal of Solid-State Circuits, vol. 42, No. 1, Jan. 2007.

Amit Ranjan Trivedi, et al, "Exploring Tunnel-FET for Ultra Low Power Analog Applications: A Case Study on Operational Transconductance Amplifier," DAC'13, May 29-Jun. 7, 2013, Austin, TX.

Reid R. Harrison, et al, "A Low-Power Low-Noise CMOS Amplifier for Neural Recording Applications," IEEE Journal of Solid-State Circuits, vol. 38, No. 6, Jun. 2003.

Woradorn Wattanapanitch, et al, "An Energy-Efficient Micropower Neural Recording Amplifier," IEEE Transactions on Biomedical Circuits and Systems, vol. 1, No. 2, Jun. 2007.

Huichu Liu et al., "Tunnel FET-Based Ultra-Low Power, Low-Noise Amplifier Design for Bio-Signal Acquisition," ISLPED '14, Aug. 11-13, 2014, La Jolla, CA.

* cited by examiner

AMPLIFIERS INCLUDING TUNABLE TUNNEL FIELD EFFECT TRANSISTOR PSEUDO RESISTORS AND RELATED DEVICES

CROSS-REFERENCE TO RELATED APPLICATION

The present application claims priority under 35 U.S.C. §119 to U.S. Provisional Application Ser. No. 62/163,533, filed on May 19, 2015, the entire content of which is incorporated herein by reference as if set forth in its entirety.

FIELD

The inventive concepts generally relate to semiconductor devices and, more particularly, to amplifiers having feedback networks that include resistors and to transistor-based pseudo resistors that can be used in these feedback networks.

BACKGROUND

The rapid growth of Internet-of-Things applications in which a wide variety of objects are provided network connectivity to allow the objects to send and/or receive data over the Internet is leading to the development of a new generation of integrated circuits that are suitable for these Internet-of-Things applications. In many cases, Internet-of-Things applications require semiconductor integrated circuits that have small layout areas, low manufacturing cost and/or low standby and operating power coupled typically with moderate computing performance (e.g., in terms of data storage, processing speed and/or connectivity).

SUMMARY

Pursuant to embodiments of the inventive concepts, amplifiers are provided that include an operational amplifier and a feedback network coupled between an output of the operational amplifier and an input of the operational amplifier, the feedback network including a first tunnel field effect transistor ("TFET") pseudo resistor. The first TFET pseudo resistor comprises a source region having a first conductivity type, a drain region having a second conductivity type that is different from the first conductivity type, a channel region having the first conductivity type between the source region and the drain region, a gate electrode on the channel region, and an electrical connection between the drain region and the gate electrode. The first TFET pseudo resistor may be configured to exhibit bi-directional conductivity. The amplifier may be a neural signal amplifier.

In some embodiments, the first TFET pseudo resistor may be tunable over at least four orders of magnitude of resistance values for an applied voltage range of –0.3 volts to 0.3 volts.

In some embodiments, the first TFET pseudo resistor may tunable over at least four orders of magnitude of resistance values, and wherein over the five orders of magnitude of resistance values, the sum of the negative applied voltage and the positive applied voltage that achieves each resistance value in the range is less than 0.12 volts In some embodiments, the feedback network may include a first capacitor coupled between an output of the operational amplifier and a first input of the operational amplifier. The first TFET pseudo resistor and a second TFET pseudo resistor may be coupled in series with each other and coupled in parallel to the first capacitor. The feedback network may also include a second capacitor coupled to a second input of the operational amplifier, and a third TFET pseudo resistor and a fourth TFET pseudo resistor that are coupled in series with each other and coupled to the second input In some embodiments, the first TFET pseudo resistor further comprises a source pocket region having the second conductivity type between the source region and the channel region. In such embodiments, the first TFET pseudo resistor may include a lightly-doped region between the source region and the source pocket region. The lightly-doped region may have a first dopant concentration that is at least two orders of magnitude less than a second doping concentration of the source region and at least two orders of magnitude less than a third doping concentration of the source pocket region. The lightly-doped region may extend further into the semiconductor substrate from a top surface of the semiconductor substrate than does the source region and/or may extend underneath the source region. The source region may form a first homojunction with the lightly-doped region, the source pocket region may form a second homojunction with the channel region, and the lightly-doped region may form a heterojunction with the source pocket region.

In some embodiments, the amplifier may include a semiconductor substrate having the first conductivity type, a first well having the second conductivity type on the semiconductor substrate and a second well having the first conductivity type on the first well opposite the semiconductor substrate, wherein the channel region is in the second well.

Pursuant to further embodiments of the inventive concepts, neural signal amplifiers are provided that include an operational amplifier and a feedback network coupled between an output of the operational amplifier and an input of the operational amplifier, the feedback network including a first tunnel field effect transistor ("TFET") pseudo resistor, where the first TFET pseudo resistor is configured to exhibit bi-directional conductivity and is tunable over at least four orders of magnitude of resistance values for an applied voltage range of –0.3 volts to 0.3 volts.

In some embodiments, over the four orders of magnitude of resistance values, the sum of the negative applied voltage and the positive applied voltage that achieves each resistance value in the range is less than 0.12 volts.

In some embodiments, the feedback network comprises a first capacitor coupled between the output of the operational amplifier and a first input of the operational amplifier, a second capacitor coupled between a second input of the operational amplifier and ground and second, third and fourth TFET pseudo resistors. In such embodiments, the first and second TFET pseudo resistors may be coupled in series with each other and coupled in parallel to the first capacitor, and the third and fourth TFET pseudo resistors may be coupled in series with each other and coupled in parallel to the second capacitor.

In some embodiments, the first TFET pseudo resistor may include a source region having a first conductivity type, a drain region having a second conductivity type that is different from the first conductivity type, a channel region having the first conductivity type between the source region and the drain region, a gate electrode on the channel region, and an electrical connection between the drain region and the gate electrode. The first TFET pseudo resistor may also include a source pocket region having the second conductivity type between the source region and the channel region. The first TFET pseudo resistor may further include a lightly-doped region between the source region and the source pocket region, wherein the lightly-doped region has a first dopant concentration that is at least two orders of magnitude less than a second doping concentration of the source region and at least two orders of magnitude less than a third doping concentration of the source pocket region In some embodiments, the source region may form a first homojunction with the lightly-doped region, the source pocket region may form a second homojunction with the channel region, and the lightly-doped region may form a heterojunction with the source pocket region.

Pursuant to yet further embodiments of the inventive concepts, tunnel field effect transistors ("TFET") are provided that include a semiconductor substrate, a source region having a first conductivity type on the semiconductor substrate, a drain region having a second conductivity type that is different from the first conductivity type on the semiconductor substrate, a channel region having the first conductivity type between the source region and the drain region, a gate electrode on the channel region opposite the semiconductor substrate, and an electrical connection between the drain region and the gate electrode to provide a TFET pseudo resistor.

In some embodiments, the TFET further includes a source pocket region having the second conductivity type between the source region and the channel region. The source pocket region may be at least partly underneath the gate electrode. The TFET may further include a lightly-doped region is provided between the source region and the source pocket region. The lightly-doped region may have a first dopant concentration that is at least two orders of magnitude less than a second doping concentration of the source region and at least two orders of magnitude less than a third doping concentration of the source pocket region. The lightly-doped region may extend further into the semiconductor substrate from a top surface of the semiconductor substrate than does the source region. The lightly-doped region may also extend underneath the source region.

In some embodiments, the source region may form a first homojunction with the lightly-doped region, the source pocket region may form a second homojunction with the channel region, and the lightly-doped region may form a heterojunction with the source pocket region.

In some embodiments, the TFET may further include a first well having the second conductivity type on the semiconductor substrate and a second well having the first conductivity type on the first well opposite the semiconductor substrate, where the channel region is part of the second well.

In some embodiments, the semiconductor substrate is a silicon substrate, and the source region includes germanium, and the source pocket region and the channel region do not include germanium. The gate electrode may be a stressed polysilicon or metal gate electrode that is configured to impart a stress on at least a portion of the source region. The TFET may also include a stressed silicon nitride layer on the source region between the gate electrode and a source contact.

In some embodiments, the TFET pseudo resistor is a first TFET pseudo resistor and is in combination with a second TFET pseudo resistor, an operational amplifier, and first and second capacitors, the first TFET pseudo resistor and the first capacitor coupled in parallel between an output of the operational amplifier and a first input to the operational amplifier, and the second TFET pseudo resistor and the second capacitor coupled in parallel between a second input of the operational amplifier and ground.

DETAILED DESCRIPTION

Figure 1:
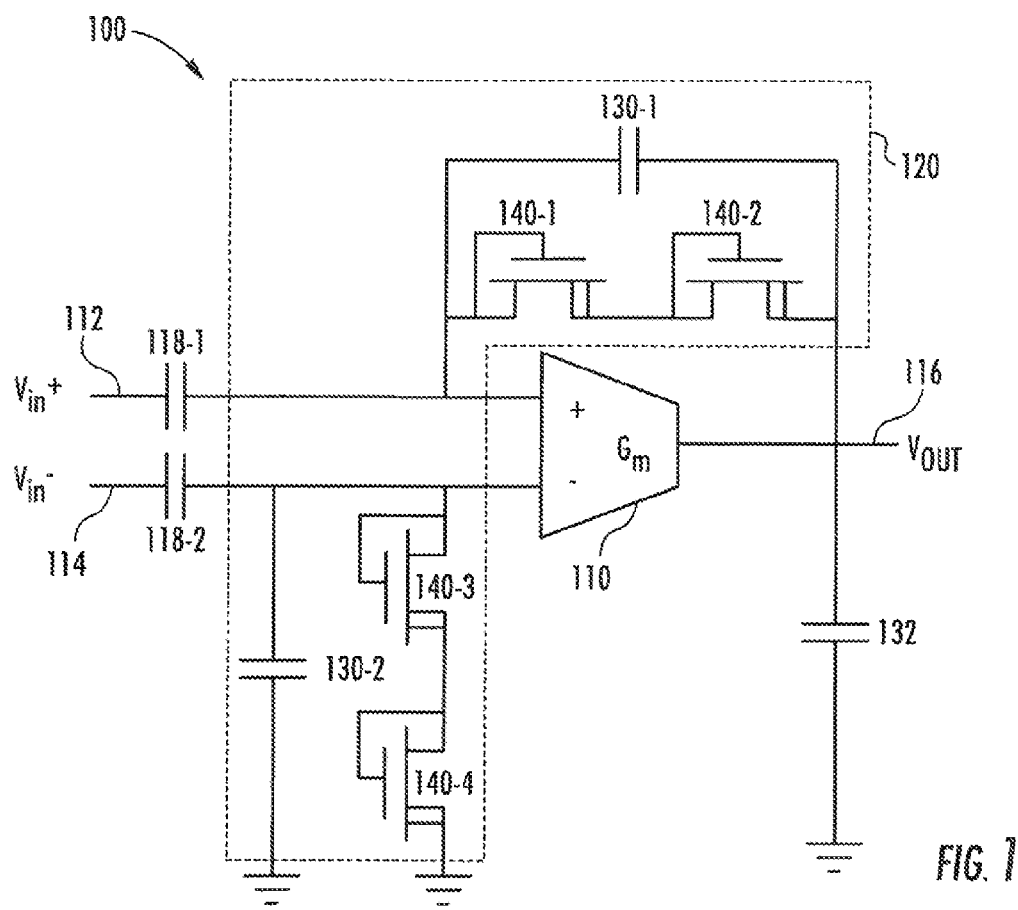
FIG. 1 is a circuit schematic of a conventional neural signal amplifiers.

Pursuant to embodiments of the inventive concepts, integrated circuit amplifiers are provided that may have a small form factor, ultra-low power consumption and improved performance. These amplifiers are suitable for use as neural signal amplifiers that are used in brain-machine interface devices. Brain-machine interface devices refer to integrated circuit chips that are implanted within the skull of an individual and are used to simultaneously record the activity of a large number of neurons. The brain-machine interface devices may include arrays of microelectrodes that are used to simultaneously record dozens, hundreds or even thousands of neural signals. Because the neural signals are weak (e.g., on the order of 10 to 500 microvolts), brain-machine devices typically include a so-called integrated neural signal amplifier that is used to amplify the recorded signals prior to processing.

A typical neural signal amplifier comprises a standard, wide-output swing operational transconductance amplifier that includes a negative-feedback resistor-capacitor ("RC")

network. The RC network may have tunable resistance values to help achieve a desired gain and operating bandwidth. As the number of recording sites, and hence the number of neural signal amplifiers that are included in the integrated circuit chip increases, it has become necessary to implement the RC network using integrated circuit capacitors and resistors in light of the size limitations on brain-machine interface devices. Another reason for using an integrated circuit approach is to minimize noise. Typical neural signals have frequencies on the order of about 100 Hz to about 7 kHz, although some neural signals may have frequencies below 1 Hz. Because of limits on the capacitance of small form factor integrated circuit capacitors (e.g., on the order of 1 pF), the resistors in neural signal amplifier designs may need to be tunable over a wide resistance range such as, for example, $10^9$ ohms to $10^{14}$ ohms. Moreover, because of the ultra low power requirements, this tunable resistance range should be achievable over a small applied voltage range.

Conventional neural signal amplifiers have typically used so-called "pseudo resistors" in the RC negative feedback networks thereof. A pseudo resistor refers to a transistor that is configured as a two-terminal device that generally functions like a resistor. Pseudo resistors may be "tunable" devices in that the resistance thereof may vary based on the voltage applied across the device.

One type of pseudo resistor that has been proposed for use in neural signal amplifiers is a MOS-bipolar pseudo resistor, which is a bi-directional device that has resistance levels that can be tuned over a fairly wide range. However, in order to suppress leakage current and meet the extended resistance range that is necessary for many neural signal amplifier applications, such MOS-bipolar pseudo resistors may require very long gate lengths, and hence may require an excessive amount of layout area in the integrated circuit chip. Moreover, the resistance of such MOS-bipolar pseudo resistors may be asymmetric with respect to the polarity of the voltage applied across the device. Accordingly, MOS-bipolar pseudo resistors may limit the integration density and/or may introduce performance distortions when used in neural signal amplifier applications.

The use of TFET pseudo resistors has also been proposed for implementing the resistors in the RC negative feedback network of a neural signal amplifier. However, the proposed TFET pseudo resistors do not support bi-directional operation, and hence the neural signal amplifiers using such TFET pseudo resistors have used twice as many pseudo resistors as the above-discussed neural signal amplifiers using MOS-bipolar pseudo resistors, which increases the layout area required to implement the neural signal amplifier and also increases the power requirements thereof. Additionally, the TFET pseudo resistors used in this proposed neural signal amplifier are generally not tunable or at most tunable over a very limited range of resistance values, and hence cannot tune over the range necessary to meet the gain and bandwidth requirements for state-of-the-art neural signal amplifier applications.

Pursuant to embodiments of the present invention, TFET pseudo resistors are provided that are tunable over a wide resistance range in response to small applied voltages. The TFET pseudo resistors according to embodiments of the present invention may occupy a very small layout area on an integrated circuit chip, and can provide improved symmetry in resistance values as a function of voltage polarity as compared to conventional MOS-bipolar pseudo resistors. Neural signal amplifiers and other amplifiers that include the TFET pseudo resistors according to embodiments of the inventive concepts are also disclosed herein.

Figure 2:
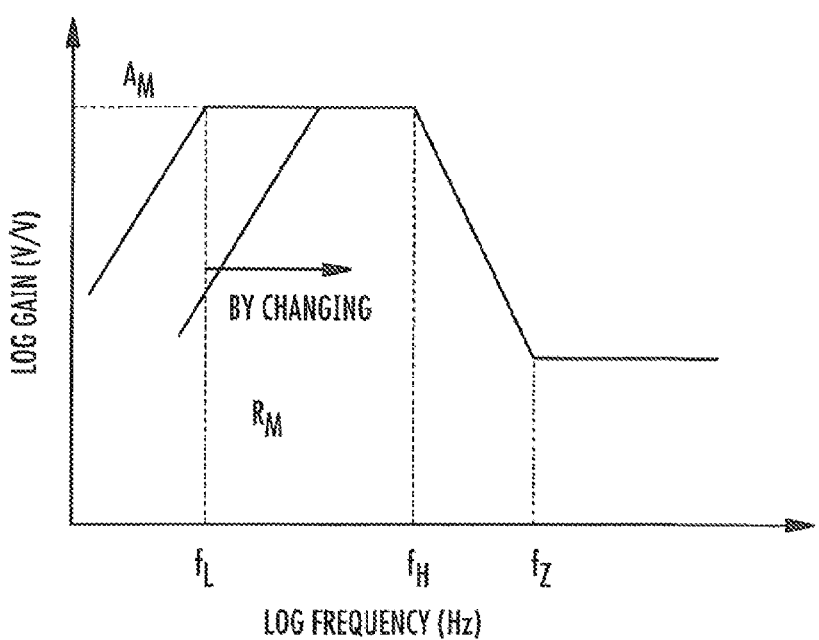
FIG. 2 is a schematic graph showing the idealized gain of the neural signal amplifier of FIG. 1 as a function of frequency.

FIG. 1 is a circuit schematic of a conventional neural signal amplifier 100. FIG. 2 is a cross-sectional diagram of a MOS-bipolar pseudo resistor that is included in an RC negative-feedback network of the neural signal amplifier 100 of FIG. 1.

As shown in FIG. 1, the neural signal amplifier 100 includes an operational amplifier 110 having first and second differential inputs 112, 114 and an output 116. A respective DC-block capacitor 118-1, 118-2 is provided at each of the differential inputs 112, 114. A load capacitor 132 is provided in series between the output 116 of operational amplifier 110 and a reference voltage such as ground. The neural signal amplifier 100 further includes an RC negative-feedback network 120. The RC negative feedback network 120 includes a first feedback capacitor 130-1 and a series pair of tunable MOS-bipolar pseudo resistors 140-1, 140-2 that are disposed in parallel between the output 116 and the inverting input 112 of the operational amplifier 110. The RC negative feedback network 120 further includes a second feedback capacitor 130-2 and a series pair of tunable MOS-bipolar pseudo resistors 140-3, 140-4 that are disposed in parallel between the non-inverting input 114 of the operational amplifier 110 and ground. Typically, the DC-block capacitors 118-1, 118-2 will have the same capacitance (C) values (i.e., $C_{118-1}=C_{118-2}$), the feedback capacitors 130-1, 130-2 will have the same capacitance values (i.e., $C_{130-1}=C_{130-2}$), and each of the MOS-bipolar pseudo resistors 140 will have the same resistance (R) value (i.e., $R_{140-1}=R_{140-2}=R_{140-3}=R_{140-4}$).

FIG. 2 is a schematic graph showing the idealized gain of the neural signal amplifier 100 of FIG. 1 as a function of frequency. As shown in FIG. 2, the neural signal amplifier 100 has a relatively constant gain (referred to herein as the midband gain $A_M$) between a low cut-off frequency $f_L$ and a high cut-off frequency $f_H$, and the gain is reduced to zero at a zero frequency $f_Z$.

The transfer function for a signal amplifier is as follows:

$$H(s,v)=v_{out}/[v_{in}^+ - v_{in}^-] \quad (1)$$

For the neural signal amplifier 100 of FIG. 1, the transfer function can be derived as shown in Equation (2):

$$H(s,v)=[C_{118-1}/C_{130-1}]*[1-s*C_{130}/G_M]/[(1+(1/(s*C_{130}*2R(v))*(1+(C_{118-1}*C_{132})/(C_{130-1}*G_M))] \quad (2)$$

In Equation (2), $G_M$ is the transconductance of the operational amplifier 110, $R_M(v)$ is the sum of the resistance values of resistors 140-1 and 140-2 (i.e., $R_{140-1}+R_{140-2}$), and s is the complex number frequency. Equation (2) may be simplified as follows:

$$H(s,v)=[A_M]*[1-(s/2\pi f_Z)]/[(1+(2\pi f_L)/s)*(1+(s/2\pi f_H))] \quad (3)$$

In Equation (3), the midband gain $A_M$ is set by the ratio of $C_{118}/C_{130}$. As noted above, $C_{118-1}$ is set to be equal to $C_{118-2}$ (herein $C_{118}$) and $C_{130-1}$ is set to be equal to $C_{130-2}$ (herein $C_{130}$). In Equation (3), the poles $f_H$ and $F_L$ and the zero frequency $f_Z$ are set as follows:

$$f_H=G_M/[2\pi*C_{132}*A_M] \quad (4)$$

$$f_L=1/[2\pi*C_{130}*R_M] \quad (5)$$

$$f_Z=f_H*C_{118}*C_{132}/C_{130}^2 \quad (6)$$

As shown in Equation (2) above, the resistance value $R_M$ of each MOS-bipolar pseudo resistor 140 is a function of the voltage applied across the resistor 140. As shown in Equation (5), the low cut-off frequency $f_L$ is a function of $R_M$, and hence the bandwidth of the linear signal amplifier 100 adjusts as a function of the voltage applied to the MOS-bipolar pseudo resistors 140. Typically, $f_Z$ can be pushed to a frequency that is beyond the highest frequency in the desired operating bandwidth for the neural signal amplifier by setting $C_{130} \ll (C_{118} * C_{130})$.

Figure 3:
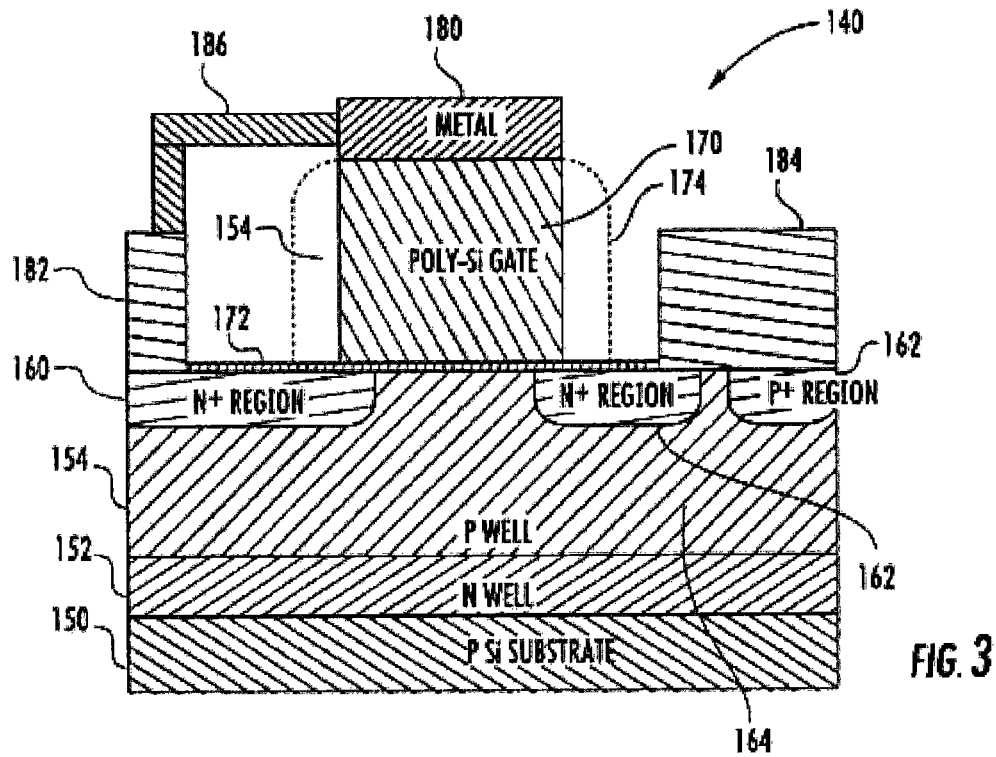
FIG. 3 is a cross-sectional diagram of a MOS-bipolar pseudo resistor that is included in the neural signal amplifier of FIG. 1.

FIG. 3 is a cross-sectional diagram of one of the MOS-bipolar pseudo resistors 140 that is included in the neural signal amplifier 100 of FIG. 1.

As shown in FIG. 3, the MOS-bipolar pseudo resistor 140 comprises a metal-oxide-semiconductor ("MOS") field effect transistor ("FET") that is formed on a silicon substrate 150. In the depicted embodiment the substrate 150 is doped to have p-type conductivity. A first well region 152 having a conductivity type that is opposite the conductivity type of the substrate 150 is formed on a top surface of the substrate 150. The first well region 152 may comprise, for example, an epitaxial grown silicon layer, and has n-type conductivity in the example of FIG. 3. A second well region 154 having a conductivity type that is the same as the conductivity type of the substrate 150 is formed on a top surface of the first well region 152. The second well region 154 may comprise, for example, a second epitaxial grown silicon layer, and has p-type conductivity in the example of FIG. 3. The first and second well regions 152, 154 may be doped during growth or may be doped by ion implantation after growth.

A drain region 160 and a source region 162 are formed on an upper portion of the second well region 154. The drain and source regions 160, 162 may comprise regions in the upper surface of the second well region 154 that are heavily doped with opposite conductivity type impurities. As shown in FIG. 3, in the depicted device, the second well region 154 is a p-type region and the drain and source regions 160, 162 are heavily doped with n-type dopants. A channel region 164 is provided in the p-type well region 154 between the drain and source regions 160, 162. A heavily-doped p-type region 166 is also provided in the upper surface of the second well region 154 adjacent the source region 162 opposite the channel region 164. A gate electrode 17Q is provided on the channel region 164, and a gate insulating layer 172 is provided between the gate electrode 170 and the channel region 164. Gate spacers 174 are provided on sidewalls of the gate electrode 170, and a gate contact 180 is formed on the gate electrode 170. A drain contact 182 is provided on the drain region 160, and a source contact 184 is provided on both the source region 162 and the heavily-doped p-type region 166. Additionally, the drain contact 182 is electrically connected to the gate contact 180 by, for example, a conductive interconnect 186 to configure the device 140 as a two-terminal MOS-bipolar pseudo resistor 140.

The MOS-bipolar pseudo resistor 140 may operate as follows. When the voltage $V_D$ that is applied to the drain contact 182 exceeds the voltage $V_S$ that is applied to the source contact 184 (i.e., $V_D > V_S$), the device 140 exhibits the behavior of a saturated MOSFET transistor with $V_D$ equal to the gate voltage $V_G$. Conversely, when $V_S > V_D$, then the device 140 acts as a p-n diode, and thus the MOS-bipolar pseudo resistors 140 will act as bi-directional devices. The resistance of the MOS-bipolar pseudo resistor 140 is a function of the voltage difference across the device (i.e., a function of $|V_D - V_S|$).

Figure 4:
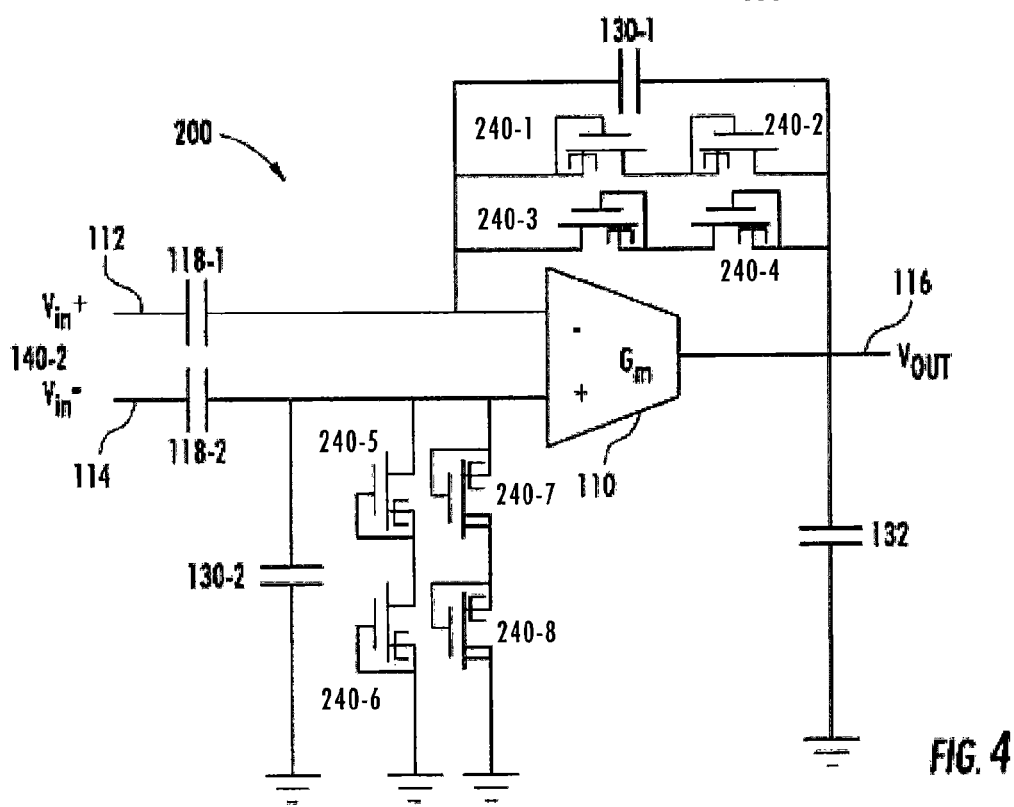
FIG. 4 is a circuit schematic of another conventional neural signal amplifier.

FIG. 4 is a circuit schematic of another conventional neural signal amplifier 200. As shown in FIG. 4, the neural signal amplifier 200 has a similar structure to the neural signal amplifier 100 described above with reference to FIG. 1. The neural signal amplifier 200 uses TFET pseudo resistors 240 each of which have the gate thereof short-circuited to a source region thereof to provide a two-terminal device. Because of this design, the gate overdrive voltage ($V_G - V_S$) is always equal to zero, and hence two parallel paths are required for bi-directional operation. Thus, as shown in FIG. 4, two paths that each have a series pair of pseudo resistors 240-1, 240-2; 240-3, 240-4 are provided in parallel to the first feedback capacitor 130-1. The pseudo resistors 240-1, 240-2 in the first of the two paths are in the opposite orientation from the pseudo resistors 240-3, 240-4 in the second of the two paths in order to support bi-directional operation. Likewise two paths that each have a series pair of pseudo resistors 240-5 through 240-8 are provided in parallel to the second feedback capacitor 130-2 and the pseudo resistors 240-5 through 240-8 that are included in each of these two paths again have opposite orientations to support bi-directional conduction. The remaining elements of the neural signal amplifier 200 may be identical to the corresponding elements in the neural signal amplifier 100 (although the values of the capacitors will be different), and hence further description thereof will be omitted.

Figure 5:
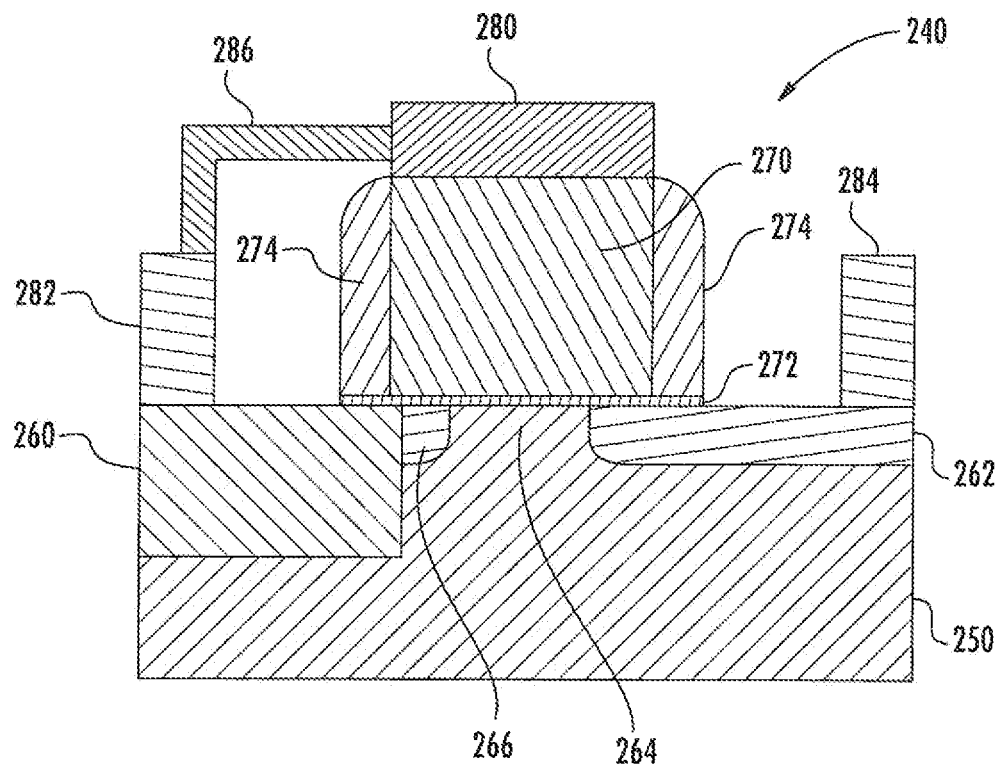
FIG. 5 is a cross-sectional diagram of a tunnel-field effect transistor ("TFET") pseudo-resistor that is included in the neural signal amplifier of FIG. 4.

FIG. 5 is a cross-sectional diagram of one of the TFET pseudo resistors 240 that is included in the neural signal amplifier 200 of FIG. 4. As shown in FIG. 5, the TFET pseudo resistor 240 comprises a tunnel field effect transistor that is formed on a semiconductor substrate 250. In the depicted embodiment the substrate 250 is doped to have p-type conductivity. A source region 260 and a drain region 262 are formed on an upper portion of the substrate 250. The source region 260 may comprise an epitaxially grown semiconductor layer that is formed in a recess in the semiconductor substrate 250. The source region 260 comprises a semiconductor material having a narrower bandgap than the semiconductor material included in the semiconductor substrate 250. The source region 260 may be heavily doped with the same conductivity type impurities as the substrate 250.

A drain region 262 is also provided on the semiconductor substrate 250. The drain region 262 may be formed of the same semiconductor material as the semiconductor substrate 250 and may be heavily doped with impurities having the opposite conductivity type of the impurities included in the semiconductor substrate 250. A channel region 264 that has the same conductivity-type as the semiconductor substrate 250 is provided between the source and drain regions 260, 262. A source pocket region 266 that is heavily-doped with the same conductivity type impurities as the drain region 262 is provided between the source region 260 and the channel region 264.

A gate electrode 270 is provided on the channel region 264, and a gate insulating layer 272 is provided between the gate electrode 270 and the channel region 264. Gate spacers 274 are provided on sidewalls of the gate electrode 270, and a gate contact 280 is formed on the gate electrode 270. A source contact 282 is provided on the source region 260, and a drain contact 284 is provided on the drain region 262. The source contact 282 is electrically connected to the gate contact 280 by, for example, a conductive interconnect 286.

Figure 6:
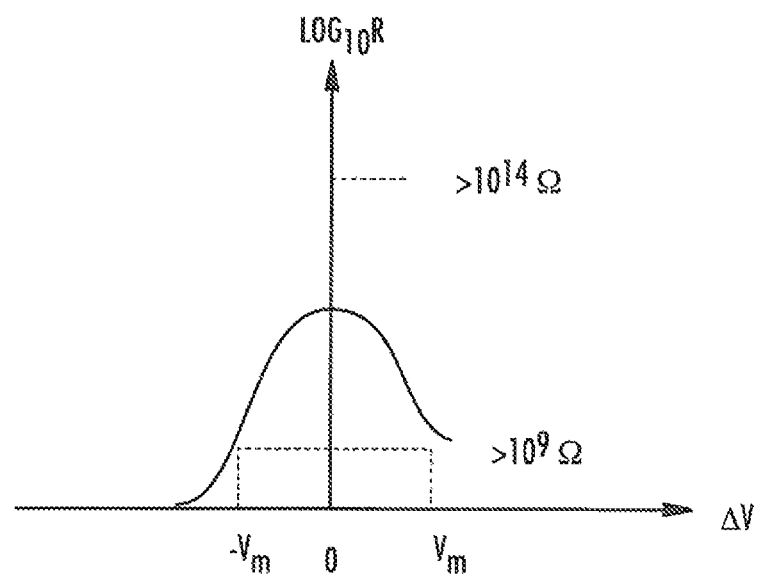
FIG. 6 is a graph that illustrates various limitations of the MOS-bipolar pseudo resistors that are included in the neural signal amplifier of FIG. 1.

The above-described neural signal amplifiers 100 and 200 have various shortcomings. For example, as shown in FIG. 6, the MOS-bipolar pseudo resistors 140 included in the neural signal amplifier 100 have an asymmetric change in resistance as a function of the applied voltage. This asymmetric resistance characteristic arises because of the degraded controllability of the gate from capacitive coupling in the device as compared to the control in a current controlled device. As is also shown in FIG. 6, the MOS-bipolar pseudo resistors 140 are not tunable across the full resistance range of $10^9$ to $10^{14}$ ohms that may be desired for neural signal amplifiers for various brain-machine interface devices. The MOS-bipolar pseudo resistors 140 may also have a relatively flat change in resistance as a function of applied voltage, and hence limitations on the applied voltage due to power consumption and heat generation may further limit the tunability of the MOS-bipolar pseudo resistors 140 across the target resistance range. Moreover, in order to maintain a low leakage current and a high threshold voltage, the gate length of the MOS-bipolar pseudo resistors may need to be on the order of 500 nm with a minimum 650 nm gate pitch, which corresponds to a large layout area and necessarily limits the integration density of the neural signal amplifier, which in turn limits the number of microelectrode pairs that may be included in the brain-machine device.

The TFET pseudo resistors 240 that are used in the neural signal amplifier 200 of FIG. 4 provide a different set of shortcomings. While these TFET pseudo resistors 240 may require a reduced layout area as compared to the MOS-bipolar devices 140, as shown in FIG. 4 above, twice as many TFET pseudo resistors 240 are necessary to support bi-directional operation. Additionally, the TFET pseudo resistors 240 are not tunable over an appreciable resistance range.

Figure 7:
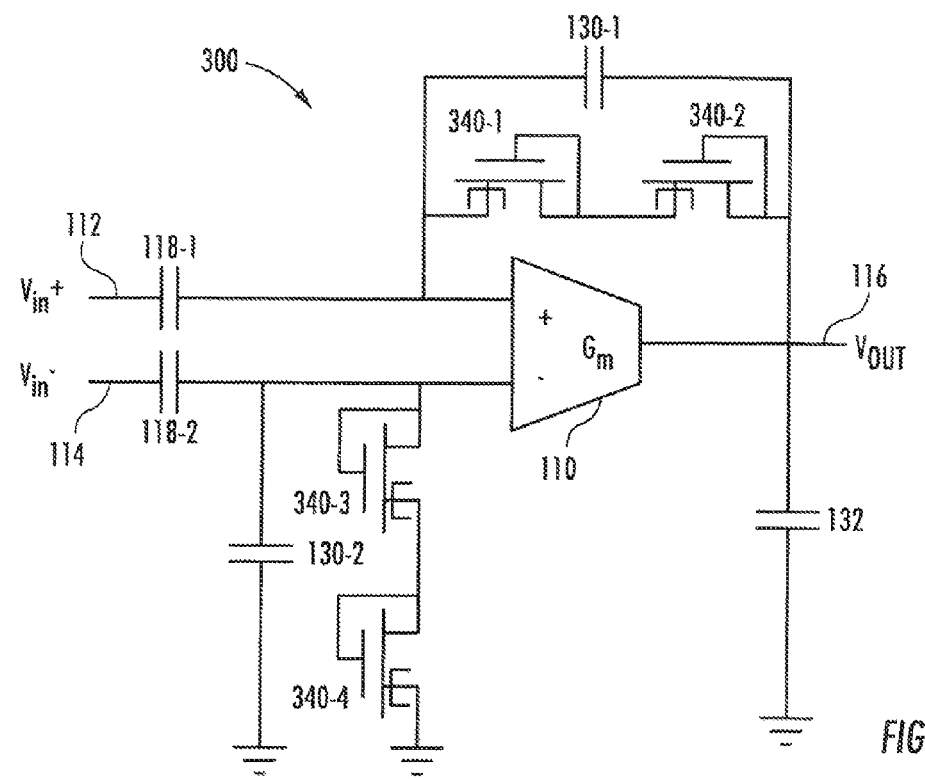
FIG. 7 is a circuit schematic of a neural signal amplifier according to embodiments of the inventive concepts.

FIG. 7 is a circuit schematic of a neural signal amplifier 300 according to embodiments of the inventive concepts. As shown in FIG. 7, the neural signal amplifier 300 may be similar to the neural signal amplifier 100 that is discussed above, but the MOS-bipolar pseudo resistors 140 that are included in amplifier 100 are replaced with tunable TFET pseudo resistors 340 in the neural signal amplifier 300. Accordingly, further description of the components of the neural signal amplifier 300 other than the tunable TFET pseudo resistors 340 will be omitted.

The neural signal amplifier 300 of FIG. 7 varies the strength of the feedback signal as a function of the magnitude of the signal being amplified, and hence is self-adaptive.

Figure 8:
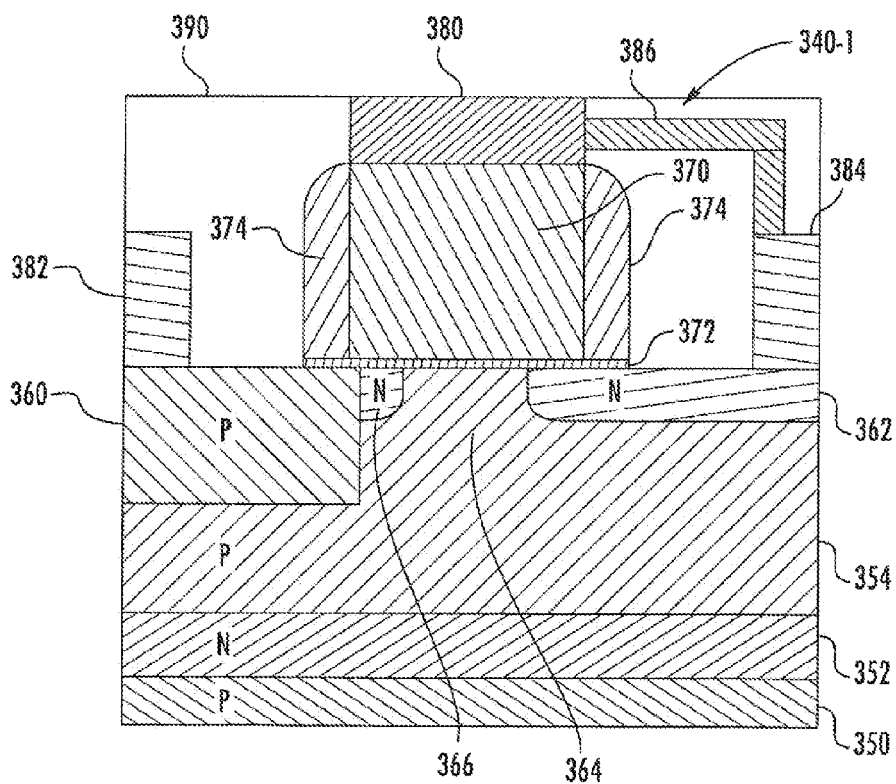
FIG. 8 is a cross-sectional diagram of a tunable TFET pseudo resistor that is included in the neural signal amplifier of FIG. 7.
Figure 9:
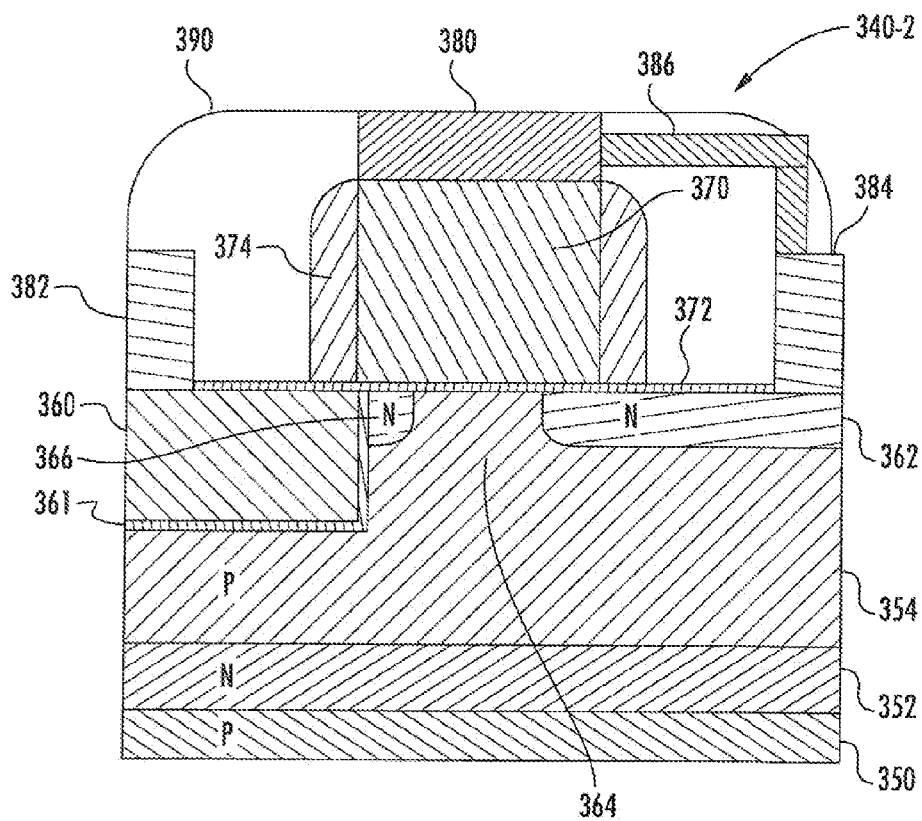
FIG. 9 is a cross-sectional diagram of tunable TFET pseudo resistor according to further embodiments of the inventive concepts that may be used in the amplifier circuit of FIG. 7.

FIGS. 8 and 9 are cross-sectional diagrams illustrating two different tunable TFET pseudo resistor designs according to embodiments of the inventive concepts.

Turning first to FIG. 8, a tunable TFET pseudo resistor 340-1 is illustrated in cross-section that has a p-n-p-n structure. As shown in FIG. 8, the tunable TFET pseudo resistor 340-1 comprises a first well 352 and a second well 354 that are sequentially formed on an underlying semiconductor substrate 350. The substrate 350 may be any appropriate semiconductor substrate such as a semiconductor wafer, a silicon-on-insulator substrate, a semiconductor layer formed on a semiconductor substrate, etc. While typically the semiconductor substrate 350 may be a silicon substrate, it will be appreciated that other semiconductor materials may be used. In the depicted embodiment, the substrate comprises a p-type silicon substrate 350, the first well 352 comprises an n-type silicon layer that is epitaxially grown on the silicon substrate 350, and the second well 354 comprises a p-type silicon layer that is epitaxially grown on the n-type silicon layer 352. The triple well structure comprising the semiconductor substrate 350, the first well 352 and the second well 354 may provide enhanced isolation that may reduce leakage currents and improve the noise figure of the neural signal amplifier 300.

A source region 360 and a drain region 362 are formed on an upper portion of the second well 354. A channel region 364 may be provided in the second well 354 between the source and drain regions 360, 362. The source region 360 may be a heavily-doped p-type source region 360, the channel region 364 may be part of the p-type second well 354, and the drain region 362 may be an n-type drain region 362. The source region 360 may comprise, for example, an epitaxially grown semiconductor layer that is formed in a recess in the second well 354. The source region 360 may be heavily doped with the same conductivity type impurities as the second well 354. The source region 360 may extend farther below a top surface of the second well 354 than the drain region 362 and/or the n-type source pocket 366 (discussed below).

In some embodiments, the p-type source region 360 may be formed of the same semiconductor material (e.g., silicon) as the semiconductor material used to form the second well 354. In other embodiments, the p-type source region 360 may comprise a semiconductor material having a narrower bandgap than the semiconductor material included in the second well 354. For example, in some embodiments, the second well 354 may a silicon layer, and the source region 36Q may comprise a silicon-germanium source region 360 that is epitaxially grown on the second well 354 using the second well 354 as a seed layer. The silicon-germanium in the source region 360 has a narrower bandgap than the silicon in the channel region 364, and hence band-to-band tunneling between the source region 360 and the channel region 364 will occur at lower gate bias voltages than the gate bias voltages at which band-to-band tunneling otherwise would occur if the source region 360 and the channel region 364 were formed of the same semiconductor material. In example embodiments, the germanium concentration in the silicon-germanium source region 360 may be between 0.25 and 0.55 by atomic weight. In other embodiments, higher germanium concentrations such as, for example, germanium concentrations greater than 0.55, or even greater than 0.8 by atomic weight may be used. In alternative embodiments, the p-type source region 360 may be a pure germanium region, a germanium-tin (Sb) region, a silicon-germanium-tin region and/or a pure tin region.

A heavily-doped n-type source pocket 366 is provided between the p-type source region 360 and the channel region 364 in an upper portion of the second well 354. The n-type source pocket 366 may be located underneath the gate electrode 370. The n-type source pocket 366 may not extend as deeply into the second well 354 as does the source region 360. The n-type source pocket 366 may help increase band bending at a low gate voltage, and hence may reduce the turn-on voltage $V_T$ for the TFET pseudo resistor 340-1, which may help reduce the power requirements for the neural signal amplifier 300.

A drain region 362 is also provided on the second well 354. The drain region 362 may be formed of the same semiconductor material as the second well 354 and may be heavily doped with impurities having the opposite conductivity type of the impurities included in the second well 354. The drain region 362 may be shallower than the source region 360. The drain region 362 may extend part of the way underneath the gate electrode 370 (which is described below). In some embodiments, the drain region 362 may have a relatively uniform doping concentration along a direction parallel to a bottom surface of the semiconductor substrate 350. The drain region 362 may be formed, for example, by ion implantation.

A gate electrode 370 is provided on the channel region 364. The gate electrode 370 may comprise, for example, a polysilicon or metal gate electrode. In some embodiments, the gate electrode 370 may be a strained polysilicon or metal gate electrode 370. The polysilicon gate electrode 370 may be strained by implanting arsenic atoms into the polysilicon using a high energy ion implantation technique, and then annealing the resultant structure. For example, arsenic atoms may be implanted into the polysilicon gate electrode 370 at an implant energy of 10-100 keV, and then the structure may be annealed at 1000-1100° C. for about 1-10,000 milliseconds. A gate insulating layer 372 is provided between the gate electrode 370 and the channel region 364. The gate insulating layer 372 may be any appropriate insulating layer such as, for example, a silicon oxide layer, a silicon-oxynitride (SiON) layer and/or a high dielectric constant material such as, for example, hafnium oxide. Gate spacers 374 are provided on sidewalls of the gate electrode 370. The gate spacers 374 may comprise, for example, silicon nitride spacers. A metal gate contact 380 is formed on the gate electrode 370. A metal source contact 382 is provided on the source region 360, and a metal drain contact 384 is provided on the drain region 362. The drain contact 384 is electrically connected to the gate contact 280 by, for example, a conductive interconnect 386. The contacts 380, 382, 384 may be ohmic metal contacts. The metal gate contact 380 may impart stress on the polysilicon gate electrode 370 that strains the underlying channel region 364 and the source region 360.

A stressed contact liner 390 may be provided on the source region 360, the drain region 362 and the gate spacers 374. The stressed contact liner 390 may comprise an amorphous silicon nitride layer. The stressed contact liner 390 may be formed by a low-temperature deposition process. The stressed contact liner 390 may be a contact etch stop liner.

The application of longitudinal tensile <110> stress on the source region 360 via provision of the strained gate electrode 370 and/or the strained contact liner 390 may reduce the bandgap of the source region 360, may lower the turn-on voltage for the device, which may allow the TFET pseudo resistor 340-1 to tune over the desired resistance range for a smaller range of applied voltages.

When the voltage $V_S$ that is applied to the source contact 382 exceeds the voltage $V_D$ that is applied to the drain contact 384 (i.e., $V_S > V_D$), the tunable TFET pseudo resistor 340-1 acts like a p-n diode. Conversely, when $V_D > V_S$, the tunable TFET pseudo resistor 340-1 acts as a TFET. In particular, in response to the voltage that is applied to the drain region 362 (and to the gate electrode 370, which is short-circuited to the drain region 362 by the conductive interconnect 386), electron accumulation occurs. When a sufficient bias voltage is applied to the drain/gate contacts 380, 384, the conduction band of the p-type channel region 364 may align with the valence band of the p-type source region 120. When this occurs, electrons from the valence band of the p-type source region 360 may tunnel into the conduction band of the p-type channel region 364 via a band-to-band tunneling mechanism, thereby allowing electrons to flow from the source region 360 to the drain region 362. In the case where the tunable TFET pseudo resistor 340-1 acts as a p-n diode and in the case where the tunable TFET pseudo resistor 340-1 acts as a TFET, the resistance thereof will be a function of the voltage difference across the device (i.e., a function of $|V_D - V_S|$).

FIG. 9 is a cross-sectional diagram illustrating a tunable TFET pseudo resistor 340-2 according to further embodiments of the inventive concepts that has a p-i-n-p-n structure.

As can be seen by comparing FIGS. 8 and 9, the tunable TFET pseudo resistor 340-2 differs from the tunable TFET pseudo resistor 340-1 in that it includes a lightly-doped region 361 (which may be so lightly doped as to be considered an intrinsic or "i-type" region) that is provided between the source region 360 and the source pocket 366.

The lightly-doped region 361 may comprise a $Si_{1-x}Ge_{x, x>0}$ region that is epitaxially grown using the second well 354 as a seed layer. The lightly-doped region 361 may be a relatively thin region. As shown in FIG. 9, in some embodiments, the lightly-doped region 361 may be on a sidewall of the p-type source region 360 that faces the channel region 364 and underneath a lower surface of the p-type source region 360. In other embodiments, the lightly-doped region 361 may only be on the sidewall of the p-type source region 360. In such embodiments, the, lightly-doped region 361 may extend along the entirety of the sidewall of the p-type source region 360 or may only extend along a portion of the sidewall 323 (e.g., the portion of the sidewall that is adjacent the n-type source pocket 366).

The lightly-doped region 361 may be an undoped region (meaning that no dopant atoms are intentionally introduced into this region), or may be a region that is only slightly doped (either n-type or p-type). For example, a relatively small quantity of p-type dopants may either diffuse from the p-type source region 360 into the lightly-doped region 361 or may be implanted in the lightly-doped region 361 during an ion implantation process. As a result, the lightly-doped region 361 may include a small number of p-type dopants. For purposes of this disclosure, the region 361 is considered to be an lightly-doped region if the concentration of dopants in the region 361 is at least two orders of magnitude less than the concentration of dopants in the p-type source region 360. For example, in some embodiments, the lightly-doped region 361 may have a concentration of dopants of $1 \times 10^{17}/cm^3$ or less, while the p-type source region 360 may have a concentration of dopants of at least $1 \times 10^{19}/cm^3$.

As explained in U.S. patent application Ser. No. 14/642,918, filed Mar. 10, 2015 ("the '918 application"), the provision of the lightly-doped region 361 between the source region 360 and the source pocket 366 may reduce the source-channel coupling capacitance. The sub-threshold swing of the TFET pseudo resistor 340 is a function of the source-channel coupling capacitance. Thus, by reducing the source-channel coupling capacitance, the TFET pseudo resistor 340 may exhibit reduced (i.e., improved) sub-threshold swing values, which may reduce the applied voltage necessary to achieve a specified change in resistance. Thus, the provision of the lightly-doped region 361 in the TFET pseudo resistors 340 may lower the power requirements for the neural signal amplifier 300. The entire content of the '918 application is incorporated herein by reference, and it will be appreciated that the TFET transistors disclosed therein may be used as tunable TFET pseudo resistors in the amplifiers according to embodiments of the inventive concepts by electrically connecting the drain region to the gate electrode thereof.

Figure 10:
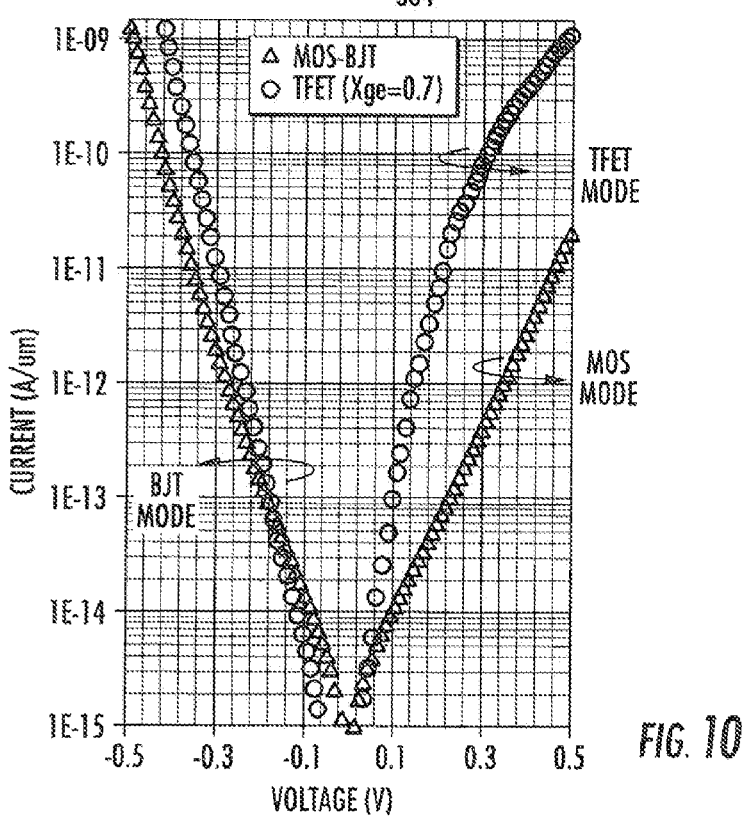
FIG. 10 is a graph of current versus voltage performance of a tunable TFET pseudo resistor according to embodiments of the inventive concepts as compared to one of the MOS-bipolar tunable resistors used in the neural signal amplifier of FIG. 1.

FIG. 10 is a graph of the simulated current as a function of the applied voltage for a MOS-bipolar pseudo resistor and a tunable TFET pseudo resistor according to embodiments of the inventive concepts. In the simulation it was assumed that each pseudo resistor was formed using a 45 nm polysilicon gate/SiON gate dielectric bulk silicon CMOS process. The simulated MOS-bipolar pseudo resistor had a 500 nm gate length, a 4.5 nm equivalent gate oxide thickness and a gate pitch of greater than 650 nm. The simulated tunable TFET pseudo resistor had a 42 nm gate length, a 1.2 nm equivalent gate oxide thickness and a gate pitch of 120 nm. The tunable TFET pseudo resistor had a $Si_{0.3}Ge_{0.7}$ source region. As shown in the graph FIG. 10, the tunable TFET pseudo resistor has more symmetric I-V behavior as compared to the MOS-bipolar pseudo resistor, and also generally achieves higher current densities at smaller applied voltages.

Figure 11:
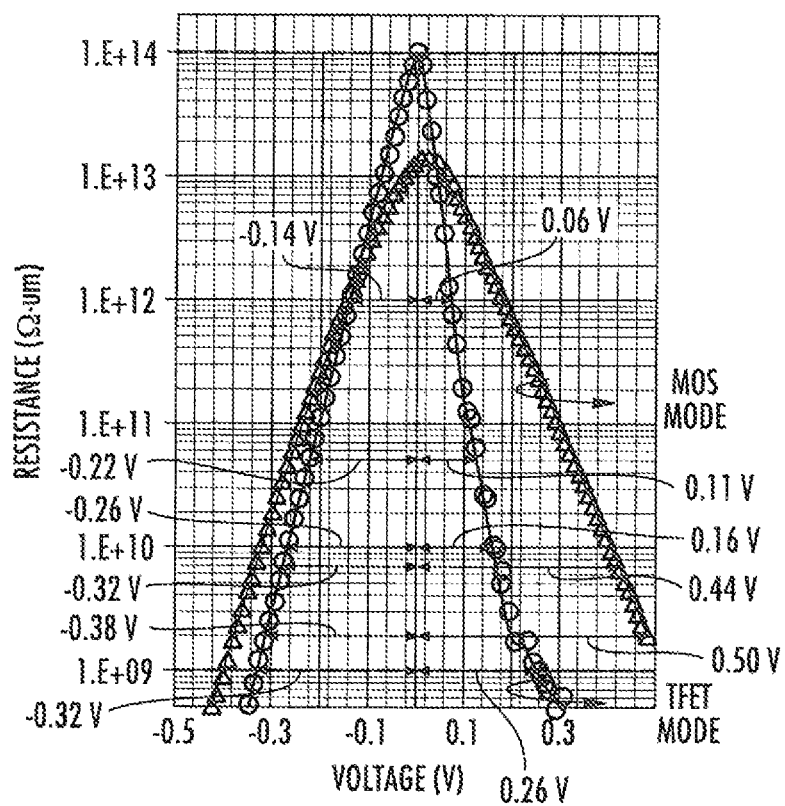
FIG. 11 is a graph of the simulated resistance as a function of the applied voltage for the above-discussed MOS-bipolar pseudo resistor and tunable TFET pseudo resistor designs used in the simulation of FIG. 10.

FIG. 11 is a graph of the simulated resistance as a function of the applied voltage for the above-discussed MOS-bipolar pseudo resistor and tunable TFET pseudo resistor designs used in the simulation of FIG. 10. As shown in FIG. 11, the tunable TFET pseudo resistor could be tuned to resistances between $10^9$ and $10^{14}$ ohms using applied voltages of less than +/−0.3 volts. In contrast, the MOS-bipolar pseudo resistor could only be tuned to resistances between $2.5 \times 10^9$ and $1.2 \times 10^{13}$ ohms using applied voltages of less than +/−0.5 volts. The graph of FIG. 11 shows that the tunable TFET pseudo resistor shows both a wider resistance tuning range within the voltage window. This may be attributable to the higher voltage swing of the TFET structure under a positive voltage bias as compared to the MOS-bipolar device. For example, the MOS-bipolar pseudo resistor may have a voltage swing of more than 90 mV per decade, as compared to a voltage swing of about 30 mV per decade for the TFET pseudo resistor.

In the graph of FIG. 11, the vertical lines corresponding to applied voltage values of −0.3 volts, −0.2 volts, −0.1 volts, 0 volts, 0.1 volts, 0.2 volts and 0.3 volts have been highlighted for clarity. Additionally, at various resistance values horizontal lines have been added along with indicators of the applied voltages necessary to achieve the resistance value for both a positive applied voltage and a negative applied voltage. As can be seen, for all resistances in the range from $10^9$ ohms to $10^{14}$ ohms the sum of the negative applied voltage and the positive applied voltage necessary to achieve each resistance value in the range is less than 0.12 volts, and is less than 0.1 volts over almost the entirety of this resistance range. This demonstrates that the TFET pseudo resistors according to embodiments of the inventive concepts exhibit good symmetry in terms of resistance as a function of the polarity of the applied voltage. In contrast, as is also shown in FIG. 11, for resistances less than about $10^{10}$ ohms, the sum of the negative applied voltage and the positive applied voltage necessary to achieve each resistance value is at least 0.12 volts. This shows that the MOS-bipolar pseudo resistors have reduced symmetry with respect to the polarity of the applied voltage, and hence neural signal amplifiers that are implemented using such MOS-bipolar pseudo resistors will exhibit increased performance degradations at lower resistance values in the target resistance range.

Figure 12:
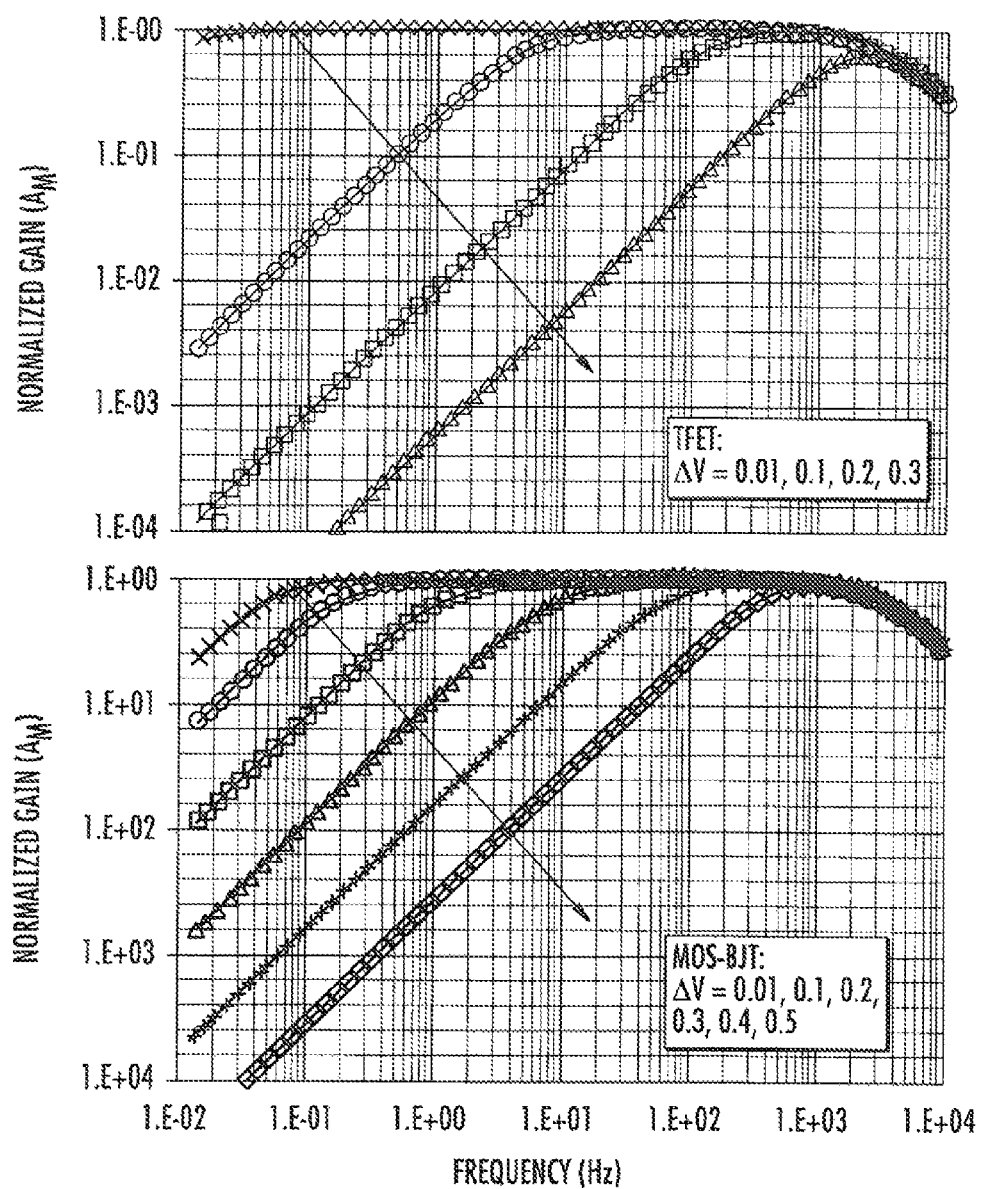
FIG. 12 includes graphs illustrating the calculated transfer functions for both the TFET and MOS-bipolar pseudo resistors used in the simulations of FIGS. 10 and 11, normalized over the midband gain $A_M$.

FIG. 12 includes graphs illustrating the calculated transfer functions for both the TFET and MOS-bipolar pseudo resistors used in the simulations of FIGS. 10 and 11, normalized over the midband gain $A_M$. In generating the graphs of FIG. 12, the following component values were used:

$C_{118-1} = C_{118-2} = 1000$ pF $C_{130-1} = C_{130-2} = 0.2$ pF $C_{132} = 100$ pF $G_M = 3$ mS

As shown in FIG. 12, the TFET pseudo resistors can tune to lower cutoff frequencies $f_L$ and can do so with smaller applied voltages as compared to the MOS-bipolar pseudo resistors.

While FIG. 7 illustrates one amplifier design according to embodiments of the inventive concepts, it will be appreciated that FIG. 7 simply illustrates one example embodiment.

Figure 13:
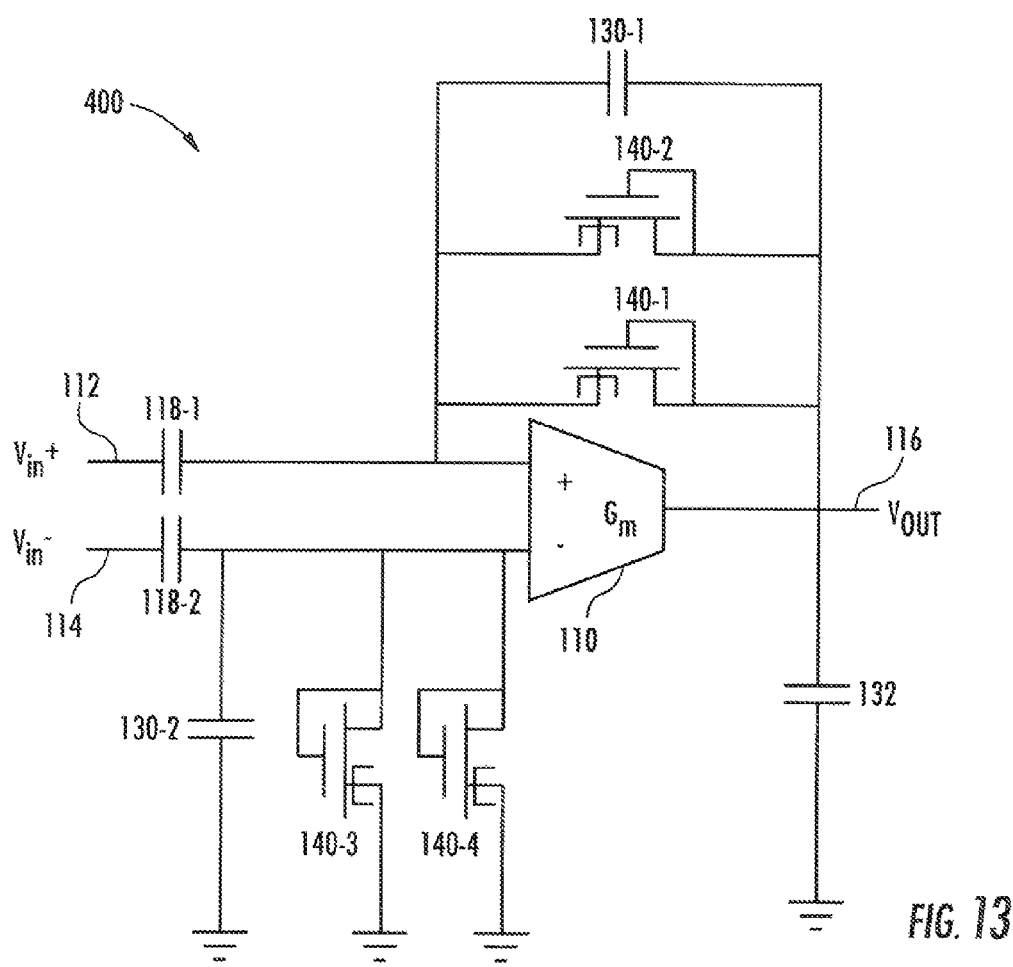
FIG. 13 is a circuit schematic of a neural signal amplifier according to further embodiments of the inventive concepts.

FIG. 13 is a circuit schematic of another amplifier 400 according to embodiments of the inventive concepts that is suitable for use as a neural amplifier. As shown in FIG. 13, the neural signal amplifier 400 is similar to the neural signal amplifier 300 of FIG. 7, except that the negative feedback circuit of the amplifier 400 places TFET pseudo resistors 140-1 and 140-2 in parallel as opposed to in series, and likewise places TFET pseudo resistors 140-1 and 140-2 in parallel as opposed to in series. As this is the only difference between the two amplifiers 300, 400, further description of the amplifier 400 will be omitted. As another example, the two resistors 140-1 and 140-2 in the amplifier 300 of FIG. 7 could be replaced with a single TFET pseudo resistor having a larger resistance value, and/or the two resistors 140-3 and 140-3 in the amplifier 300 could be replaced with a single TFET pseudo resistor having a larger resistance value.

While the above description has focused primarily on neural signal amplifiers as the amplifiers according to embodiments of the inventive concepts are well-suited to this application, it will be appreciated that the amplifiers disclosed herein may be used in other applications. The amplifiers disclosed herein are particularly well-suited to applications that require extremely low power and have resistors in a feedback network that must be tunable over a relatively wide resistance range with good symmetry as a function of voltage polarity.

While in the above description n-type TFET pseudo resistors are illustrated, it will be appreciated that p-type TFET pseudo resistors may be used in other embodiments.

Embodiments of the inventive concepts have been described above with reference to the accompanying drawings, in which example embodiments are shown. The inventive concepts may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout the drawings and specification. As used herein the expression "and/or" includes any and all combinations of one or more of the associated listed items.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present invention.

It will be understood that when an element is referred to as being "coupled to" or "connected to" or "on" another element, it can be directly coupled to, connected to or on the other element or intervening elements may also be present. In contrast, when an element is referred to as being "directly coupled to" or "directly connected to" or "directly on" another element, there are no intervening elements present. Other words used to describe the relationship between elements should be interpreted in a like fashion (i.e., "between" versus "directly between", "adjacent" versus "directly adjacent", etc.).

Relative terms such as "below" or "above" or "upper" or "lower" or "horizontal" or "vertical" may be used herein to describe a relationship of one element, layer or region to another element, layer or region as illustrated in the figures. It will be understood that these terms are intended to encompass different orientations of the device in addition to the orientation depicted in the figures.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes" and/or "including" when used in this specification, specify the presence of stated features, elements, and/or components, but do not preclude the presence or addition of one or more other features, elements, components, and/or groups thereof.

Embodiments of the inventive concepts have been described above with reference to cross-section illustrations that are schematic illustrations of idealized embodiments (and intermediate structures) of the inventive concepts. The thickness of layers and regions in the drawings may be exaggerated for clarity. Additionally, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

All embodiments can be combined in any way and/or combination.

In the drawings and specification, there have been disclosed typical embodiments of the inventive concepts and, although specific terms are employed, they are used in a generic and descriptive sense only and not for purposes of limitation, the scope of the inventive concepts being set forth in the following claims.

What is claimed is:
1. An amplifier, comprising:
    an operational amplifier; and
    a feedback network coupled between an output of the operational amplifier and a first input of the operational amplifier, the feedback network comprising a first tunnel field effect transistor ("TFET") pseudo resistor, wherein the first TFET pseudo resistor comprises:
        a source region having a first conductivity type;
        a drain region having a second conductivity type that is different from the first conductivity type;
        a channel region having the first conductivity type between the source region and the drain region;
        a gate electrode on the channel region; and
        an electrical connection between the drain region and the gate electrode,
    wherein the feedback network further comprises a first capacitor coupled between the output of the operational amplifier and the first input of the operational amplifier, and wherein the first TFET pseudo resistor and a second TFET pseudo resistor are coupled in series with each other and coupled in parallel to the first capacitor.
2. The amplifier of claim 1, wherein the first TFET pseudo resistor is configured to exhibit bi-directional conductivity.
3. The amplifier of claim 2, wherein the first TFET pseudo resistor is tunable over at least five orders of magnitude of resistance values for an applied voltage range of −0.3 volts to 0.3 volts.
4. The amplifier of claim 1, wherein the first TFET pseudo resistor is tunable over a range comprising at least four orders of magnitude of resistance values, and wherein over the at least four orders of magnitude of resistance values, a sum of a negative applied voltage and a positive applied voltage that achieves each resistance value in the range is less than 0.12 volts.
5. The amplifier of claim 1, wherein the feedback network further comprises a second capacitor coupled to a second input of the operational amplifier and a third TFET pseudo resistor and a fourth TFET pseudo resistor that are coupled in series with each other and coupled to the second input.
6. The amplifier of claim 5, wherein the amplifier comprises a neural signal amplifier.
7. The amplifier of claim 1, wherein the first TFET pseudo resistor further comprises a source pocket region having the second conductivity type between the source region and the channel region.
8. The amplifier of claim 7, wherein the first TFET pseudo resistor further comprises a lightly-doped region between the source region and the source pocket region.
9. The amplifier of claim 8, wherein the lightly-doped region has a first dopant concentration that is at least two orders of magnitude less than a second doping concentration of the source region and at least two orders of magnitude less than a third doping concentration of the source pocket region.
10. The amplifier of claim 9, wherein the lightly-doped region extends further into a semiconductor substrate from a top surface of the semiconductor substrate than does the source region.
11. The amplifier of claim 8, wherein the source region forms a first homojunction with the lightly-doped region, wherein the source pocket region forms a second homojunction or heterojunction with the channel region, and wherein the lightly-doped region forms a heterojunction with the source pocket region.
12. The amplifier of claim 1, further comprising a semiconductor substrate having the first conductivity type, a first well having the second conductivity type on the semiconductor substrate and a second well having the first conductivity type on the first well opposite the semiconductor substrate, wherein the channel region is in the second well.
13. A neural signal amplifier, comprising:
    an operational amplifier; and
    a feedback network coupled between an output of the operational amplifier and a first input of the operational amplifier, the feedback network comprising a first tunnel field effect transistor ("TFET") pseudo resistor, wherein the first TFET pseudo resistor is configured to exhibit bi-directional conductivity and is tunable over a range comprising at least four orders of magnitude of resistance values for an applied voltage range of −0.3 volts to 0.3 volts, wherein the feedback network further comprises:
        a first capacitor coupled between the output of the operational amplifier and the first input of the operational amplifier;
        a second capacitor coupled between a second input of the operational amplifier and ground; and
        second, third and fourth TFET pseudo resistors,
    wherein the first and second TFET pseudo resistors are coupled in series with each other and coupled in parallel to the first capacitor, and
    wherein the third and fourth TFET pseudo resistors are coupled in series with each other and coupled in parallel to the second capacitor.
14. The neural signal amplifier of claim 13, wherein over the at least four orders of magnitude of resistance values a sum of a negative applied voltage and a positive applied voltage that achieves each resistance value in the range is less than 0.12 volts.

15. The neural signal amplifier of claim 13, wherein the first TFET pseudo resistor comprises:
   a source region having a first conductivity type;
   a drain region having a second conductivity type that is different from the first conductivity type;
   a channel region having the first conductivity type between the source region and the drain region;
   a gate electrode on the channel region; and
   an electrical connection between the drain region and the gate electrode.

16. The neural signal amplifier of claim 15, wherein the first TFET pseudo resistor further comprises a source pocket region having the second conductivity type between the source region and the channel region.

17. The neural signal amplifier of claim 16, wherein the first TFET pseudo resistor further comprises a lightly-doped region between the source region and the source pocket region, wherein the lightly-doped region has a first dopant concentration that is at least two orders of magnitude less than a second doping concentration of the source region and at least two orders of magnitude less than a third doping concentration of the source pocket region.

18. The neural signal amplifier of claim 17, wherein the source region forms a first homojunction with the lightly-doped region, wherein the source pocket region forms a second homojunction or heterojunction with the channel region, and wherein the lightly-doped region forms a heterojunction with the source pocket region.

* * * * *